United States Patent [19]

Fishman

[11] 4,004,025
[45] Jan. 18, 1977

[54] LONG-ACTING LOCAL SUBCUTANEOUSLY-APPLIED ANESTHETICS AND COMPOSITIONS CONTAINING THE SAME

[75] Inventor: Jack Fishman, New York, N.Y.

[73] Assignees: Evalina Lewenstein; Henry Hirsch and Stanley Rothschild, trustees, all of New York, N.Y.

[22] Filed: Feb. 4, 1976

[21] Appl. No.: 655,458

Related U.S. Application Data

[60] Continuation-in-part of Ser. No. 501,131, Aug. 28, 1974, abandoned, which is a division of Ser. No. 324,823, Jan. 18, 1973, abandoned.

[52] U.S. Cl. .............................................. 424/308
[51] Int. Cl.² ..................................... A61K 31/235
[58] Field of Search .................................. 424/308

[56] References Cited

OTHER PUBLICATIONS

Pogosyan et al., Chem. Abst. vol. 63 (1965) p. 7118d.

*Primary Examiner*—Jerome D. Goldberg
*Assistant Examiner*—Allen J. Robinson
*Attorney, Agent, or Firm*—Kirschstein, Kirschstein, Ottinger & Frank

[57] ABSTRACT

Novel compounds constituting esters of benzoic acids, selected from the group consisting of p-vinyl benzoic acid and p-ethynyl benzoic acid, with an aminoethanol selected from the group consisting of diethylaminoethanol and N-substituted aminoethanols. The esters have the formula

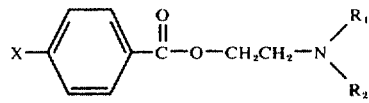

where X is selected from the group consisting of

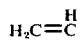

or HC ≡ C and each of $R_1$ and $R_2$ is selected from the group consisting of H, lower alkyls containing up to 6 carbon atoms and cycloalkyls. The novel compounds also include inorganic and organic acid salts of said esters. The novel compounds have a unique medicinal function as local subcutaneously-applied anesthetics which have a long-acting effect when administered without vasoconstrictors that heretofore have been used to prevent rapid dissipation of subcutaneously-applied local anesthetics. The invention also embraces compositions containing the compounds and the method of using the novel compounds and compositions as local long-acting subcutaneously-applied anesthetics.

15 Claims, No Drawings

LONG-ACTING LOCAL SUBCUTANEOUSLY-APPLIED ANESTHETICS AND COMPOSITIONS CONTAINING THE SAME

CROSS REFERENCE TO RELATED APPLICATION

This application is a continuation-in-part of copending application Ser. No. 501,131 (now abandoned) filed Aug. 28, 1974 by JACK FISHMAN for LONG-ACTING LOCAL SUBCUTANEOUSLY-APPLIED ANESTHETICS AND COMPOSITIONS CONTAINING THE SAME, which is a division of application Ser. No. 324,823 (now abandoned) filed Jan. 18, 1973 by the same inventor with the same title.

BACKGROUND OF THE INVENTION

1. Field of the Invention

A long-acting local subcutaneously-applied anesthetic.

2. Description of the Prior Art

In local subcutaneous anesthesia it currently is common practice to introduce a local anesthetic subcutaneously along with one or more vasoconstrictors. The vasoconstrictors are used in order to prevent too rapid dissipation of the anesthetic. The vasoconstrictors invariably are potentially dangerous and definitely are contraindicated in patients with heart conditions.

SUMMARY OF THE INVENTION

1. Purposes of the Invention

It is an object of the invention to provide an improved anesthetic which overcomes the foregoing drawbacks, that is to say, an anesthetic which can be introduced subcutaneously into a patient without a vasoconstrictor or combination of vasoconstrictors and which will not, when so administered, dissipate rapidly so that such anesthetic can be used on a far wider spectrum of patients without incurring dangerous side effects.

2. Brief Description of the Invention

An ester of benzoic acid, selected from the group consisting of p-vinyl benzoic acid and p-ethynyl benzoic acid, with an aminoethanol selected from the group consisting of diethylaminoethanol and N-substituted aminoethanols. The esters have the formula

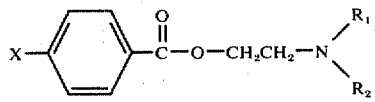

where X is selected from the group consisting of

or $HC \equiv C$ and where each of $R_1$ and $R_2$ is selected from the group consisting of H, lower alkyls containing up to 6 carbon atoms and cycloalkyls, typical ones of which are cyclopropyl, cyclobutyl and cyclohexyl, the ester being useful as a local subcutaneously-applied anesthetic which is long-acting and will not dissipate rapidly when subcutaneously applied without a vasoconstrictor or combination of vasoconstrictors. The esters are used as such or as inorganic acid or organic salts thereof. A typical inorganic salt is a hydrochloride or a sulfate salt of such an ester and a typical organic salt is an acetate or propionate salt of such an ester. The new compound, i.e. ester or salt thereof, generally is included in a composition, being incorporated in a carrier such, for instance, as sterile water including sterile distilled water, sterile isotonic water or sterile water buffered with ethanol or another suitable solvent such as is well known in the pharmaceutical art relating to subcutaneously-applied anesthetics. Also, there may be included in the composition including the novel compound and carrier an antioxidant, for example, sodium bisulfite or ascorbic acid.

A suitable dosage rate for the novel compound is from about 0.1 milligrams to about 40 milligrams per kilogram of body weight of a patient.

These compounds are useful as local anesthetics when subcutaneously applied and they function effectively in this manner without rapid dissipation, this despite the absence of vasoconstrictors that previously were employed to prevent such rapid dissipation and which gave rise to adverse side effects.

The invention consists in the compounds and compositions, steps of preparation and manners of use hereinafter described and the scope of which is indicated in the appended claims.

DESCRIPTION OF THE PREFERRED EMBODIMENTS

Generally speaking, the new anesthetic compounds can be prepared by reacting the acid chloride of the appropriate acid with the appropriate amino alcohol in an inert organic solvent to form the desired ester.

If the compounds are to be converted to salts, they are reacted with appropriate acids. Typical pharmaceutically acceptable salts of said compounds include both organic and inorganic salts such as the following:- nitrates, nitrites, iodides, iodates, bromides, bromates, phosphates, chlorates, chlorides, formates, butyrates, isobutyrates, valerates, caprolates, chloroacetates, bromoacetates, iodoacetates, dichloroacetates, trichloroacetates, lactates, methoxyacetates, glyoxylates, salicylates, oxalates, malonates, succinates, glutarates, tartrates and vinylacetates.

As mentioned previously, the new compound, which is either an ester as aforesaid or a salt thereof, preferably is diluted by inclusion of the same in a composition which at least constitutes the new compound and a carrier for the same. Any of the carriers conventionally used for diluting medicaments that are administered to a patient subcutaneously may be employed, typical ones of these being sterile distilled water, sterile distilled water with an isotonic amount of sodium chloride therein, and sterile distilled water which has been buffered with ethanol or some other suitable solvent such as is well known in the art. The dilution of the new compound in the carrier conveniently varies from 0.05 to 50 milligrams of the new compound to one cc of the carrier.

Furthermore, as set forth above, the new compound will create the desired result of obtaining anesthesia without the accompanying presence of a vasoconstrictor when subcutaneously injected in an amount ranging from about 0.1 milligrams to about 40 milligrams per kilogram of body weight of the patient.

The following are examples of methods of preparation:

EXAMPLE I

A solution of 14.8 grams of p-vinyl benzoic acid in 50 ml of benzene was refluxed at the boiling point of benzene at 760 mm. Hg pressure with 10 grams of thionyl chloride for 2 hours until no more HCl was given off. The solvent and excess reagent were removed under vacuum and the residue was taken up in 100 ml of benzene, chilled and shaken with cold 5% aqueous $NaHCO_3$ solution. The organic layer was then dried over $Na_2SO_4$ and the solvent was evaporated at 50° C at a reduced pressure of about 100 mm. Hg. The residue was taken up in 50 ml of dry benzene and was treated by a dropwise addition of 12 grams of 2-diethylaminoethanol in 50 ml of ether, with stirring at room temperature and at atmospheric pressure. After addition, stirring was continued for one-half hour. The solvents were removed at 50° C and at a reduced pressure of about 40 mm Hg. The residue was recrystallized from ethanol to give 15.8 grams of 2-diethylaminoethyl p-vinyl benzoate hydrochloride, m.p. 123°–125° C. The free basic ester is obtained by dissolving the salt in 30 ml of water, adjusting the pH to 9 with dilute sodium hydroxide solution and extracting with ether. Evaporation of the ether yielded the 2-diethylaminoethyl p-vinyl benzoate.

EXAMPLE II

A solution of 9 grams of p-vinyl benzoyl chloride in 50 ml of benzene was treated by the dropwise addition of a solution of 4.7 grams of 2-dimethylaminoethanol in 50 ml of benzene. After stirring for 20 minutes at 20° C the precipitate that was formed was filtered off, dried and recrystallized from ethanol to give 2-dimethylaminoethyl p-vinyl benzoate hydrochloride, m.p. 111°–113° C.

EXAMPLE III

A solution of 9 grams of p-vinyl benzoyl chloride in 30 ml of dry ether was treated by the dropwise addition of 5 grams of 2-ethyl isopropylaminoethanol in 25 ml of ether at 24° C. After 1 hour the precipitate that was formed was filtered off, washed with ether and recrystallized from ethanol to give 2-ethyl isopropylaminoethyl p-vinyl benzoate hydrochloride, m.p. 148°–150° C.

EXAMPLE IV

A solution of 15 grams of p-ethynyl benzoic acid in 70 ml of benzene was refluxed at 80° C with 10 grams of thionyl chloride until no more hydrogen chloride was evolved. The benzene was then washed with cold 5% $NaHCO_3$ solution, then water-dried over sodium sulfate and evaporated. The residue consisting of 15.8 grams of p-ethynyl benzoyl chloride was dissolved in 50 ml of dry benzene. A solution of 11.5 grams of 2-diethylaminoethanol in 50 ml of benzene was added slowly with stirring. After all the material was added, the stirring was continued for 1 hour, and the precipitate was filtered off and recrystallized from isopropyl alcohol to give 2-diethylaminoethyl p-ethynyl benzoate hydrochloride, m.p. 174°–176° C.

EXAMPLE V

To a solution of 11 grams of p-ethynyl benzoyl chloride in 100 ml of ethyl ether, a solution of 7 grams of 2-dimethylaminoethanol in 50 ml of ethyl ether was added with stirring at 22° C. The precipitate that was formed was filtered off and recrystallized from methanol to yield 2-dimethylaminoethyl p-ethynyl benzoate hydrochloride, m.p. 162°–164° C.

EXAMPLE VI

To a solution of 10 grams of p-vinyl benzoyl chloride in 50 ml of benzene was added slowly with stirring a solution of 5 grams of 2-piperidinoethanol in 30 ml of benzene. The precipitate that was formed was filtered and recrystallized from ethanol to give 2-piperidino ethyl p-vinyl benzoate hydrochloride, m.p. 214°–216° C.

EXAMPLE VII

A solution of 6 grams 2-morpholino ethanol in 50 ml of ether was added slowly with stirring to a solution of 90 grams of p-ethynyl benzoyl chloride in 50 ml of ether at 15° C. A precipitate that was formed was filtered and crystallized from ethanolether to give the 2morpholine ethyl p-ethynyl benzoate hydrochloride, m.p. 181°–186° C.

EXAMPLE VIII

To a solution of 28 grams of p-ethynyl benzoyl chloride in ether, 6 grams of 2(N-cyclopropylmethyl-N-ethyl) aminoethanol in ether was added slowly with stirring at 22° C. The resultant precipitate was filtered and crystallized from ethanol to give 2(N-cyclopropylmethyl-N-ethyl) aminoethyl p-ethynyl benzoate hydrochloride, m.p. 184°–188° C.

EXAMPLE IX

A solution of 4 grams of 2-diisopropyl aminoethanol in 50 ml of ether was added dropwise to a stirred solution of 20 grams of p-vinyl benzoyl chloride in 50 ml of dry ether. A precipitate was formed which was filtered and crystallized from methanol-ether to give 2-diisopropyl aminoethyl p-vinyl benzoate hydrochloride, m.p. 114°–118° C.

All of the above salts of esters can be converted to the free ester state by extraction from an alkaline water medium with an organic solvent as detailed, for instance, in connection with EXAMPLE I. Any of such free esters can be converted to any desired salt by reaction with the appropriate acid.

The new compounds of the invention when used as acid salts preferably include as a carrier an aqueous type medium such, for instance, as sterile distilled water with or without any of the adjuvants previously mentioned such as salt in an isotonic amount, a pharmaceutically acceptable organic solvent in an acceptable amount, a buffer, or an anti-oxidant, the use of these adjuvants being so well known that they need not be detailed herein, particularly since their use does not constitute a feature of the invention. The dosage level for subcutaneous injection will depend upon the judgment of the physician and, as previously pointed out, can vary quite widely from about 0.1 milligrams to about 40 milligrams per kilogram of patient body weight.

It has been observed that when compounds of the invention are applied subcutaneously to patients within the dosage levels above indicated in the absence of vasoconstrictors (either with the compound or immediately before or after application of the compound), local anesthetic effects are secured which are of long duration, the duration obviously depending upon the physiology of the patient and usually being in the order of from 3 to 5 hours. This duration is substantially in excess, approximately three times, of the duration of anesthetic effect obtained with a standard anesthetic such as Xylocaine subcutaneously applied without a vasoconstrictor.

It thus will be seen that there have been provided compounds, compositions and methods which achieve the various objects of the invention and which are well adapted to meet the conditions of practical use.

As various possible embodiments might be made of the above invention, and as various changes might be made in the embodiments above set forth, it is to be understood that all matter herein described is to be interpreted as illustrative and not in a limiting sense.

Having thus described the invention there is claimed as new and desired to be secured by Letters Patent:

1. A composition for subcutaneous administration to induce local anesthesia, said composition being in the form of an injectable solution, said composition comprising an anesthetically effective amount of a compound having the formula

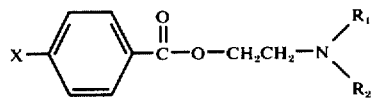

where X is selected from the group consisting of

or $HC \equiv C$ and where each of $R_1$ and $R_2$ is selected from the group consisting of H, lower alkyls containing up to 6 carbon atoms, cyclopropyl, cyclobutyl and cyclohexyl, or pharmaceutically acceptable salts thereof, and a sterile water carrier for said compound.

2. The composition as set forth in claim 1 wherein the salt of the compound is selected from the group consisting of nitrates, sulfates, nitrites, iodides, iodates, bromides, bromates, phosphates, chlorides, chlorates, chlorites, formates, butyrates, isobutyrates, valerates, caprolates, chloroacetates, bromoacetates, iodoacetates, dichloroacetates, trichloroacetates, lactates, methoxyacetates, glyoxylates, salicylates, oxalates, malonates, succinates, glutarates, tartrates and vinylacetates.

3. The composition as set forth in claim 1 wherein the compound is 2-diethylaminoethyl p-vinyl benzoate hydrochloride.

4. The composition as set forth in claim 1 wherein the compound is 2-dimethylaminoethyl p-vinyl benzoate hydrochloride.

5. The composition as set forth in claim 1 wherein the compound is 2-ethyl isopropylaminoethyl p-vinyl benzoate hydrochloride.

6. The composition as set forth in claim 1 wherein the compound is 2-diethylaminoethyl p-ethynyl benzoate hydrochloride.

7. The composition as set forth in claim 1 wherein the compound is 2-dimethylaminoethyl p-ethynyl benzoate hydrochloride.

8. The composition as set forth in claim 1 wherein the compound is 2-diisopropylaminoethyl p-vinyl benzoate hydrochloride.

9. The composition as set forth in claim 1 wherein the compound is 2-diethylaminoethyl p-vinyl benzoate.

10. The composition as set forth in claim 1 wherein the compound is 2-dimethylaminoethyl p-vinyl benzoate.

11. The composition as set forth in claim 1 wherein the compound is 2-ethylisopropylaminoethyl p-vinyl benzoate.

12. The composition as set forth in claim 1 wherein the compound is 2-diethylaminoethyl p-ethynyl benzoate.

13. The composition as set forth in claim 1 wherein the compound is 2-dimethylaminoethyl p-ethynyl benzoate.

14. The composition as set forth in claim 1 wherein the compound is 2-diisopropylaminoethyl p-vinyl benzoate.

15. A method of inducing a long-lasting local anesthetic effect in a patient consisting of injecting subcutaneously into the patient a composition as set forth in claim 1 in an amount of from about 0.1 to about 40 milligrams of the compound per kilogram of patient body weight.

* * * * *